(12) United States Patent
Hansen

(10) Patent No.: US 11,801,352 B2
(45) Date of Patent: Oct. 31, 2023

(54) DEVICES AND CONTROL SYSTEMS FOR INHALED DRUGS

(71) Applicant: Brian Hansen, Loveland, CO (US)

(72) Inventor: Brian Hansen, Loveland, CO (US)

(73) Assignee: Brian Hansen, Loveland, CO (US)

( * ) Notice: Subject to any disclaimer, the term of this patent is extended or adjusted under 35 U.S.C. 154(b) by 1022 days.

(21) Appl. No.: 16/481,883

(22) PCT Filed: Feb. 4, 2018

(86) PCT No.: PCT/US2018/016776
§ 371 (c)(1),
(2) Date: Jul. 30, 2019

(87) PCT Pub. No.: WO2018/144964
PCT Pub. Date: Aug. 9, 2018

(65) Prior Publication Data
US 2019/0351158 A1 Nov. 21, 2019

Related U.S. Application Data

(60) Provisional application No. 62/454,843, filed on Feb. 5, 2017.

(51) Int. Cl.
*A61M 15/00* (2006.01)
*A61K 31/465* (2006.01)
(Continued)

(52) U.S. Cl.
CPC .......... *A61M 15/009* (2013.01); *A24F 40/485* (2020.01); *A24F 40/50* (2020.01);
(Continued)

(58) Field of Classification Search
CPC ............ A61M 15/009; A61M 15/0066; A61M 15/008; A61M 2202/064; A61M 2205/3331; A61M 2205/3368; A61M 2205/36; A61M 2205/50; A61M 2205/502; A61M 2205/52; A61M 2205/8206; A61M 2230/42; A24F 40/485; A61K 31/465; A61K 31/498
See application file for complete search history.

(56) References Cited

U.S. PATENT DOCUMENTS 5,394,866 A * 3/1995 Ritson ................... A61M 15/00
128/200.14
5,404,871 A * 4/1995 Goodman ............... G01F 1/363
128/200.14
(Continued)

*Primary Examiner* — Steven O Douglas

(57) ABSTRACT

Inhaled medications present a great opportunity for controlled drug delivery for self medicated patients. With this invention most medicinal aerosol generators have the potential for much more controlled dosage and monitoring of doses to the patient than current inhaled medication systems. The pressurized metered dose inhaler has especially great potential for controlled drug delivery being that the aerosol drug formulation is in a permanently sealed container that can use a digital program controlled electromechanical valve on a metered dose inhaler to control drug dose and time of release. An electromechanical inhaler valve actuator can also provide dose control, monitoring, breath activation timing and other important features.

20 Claims, 1 Drawing Sheet

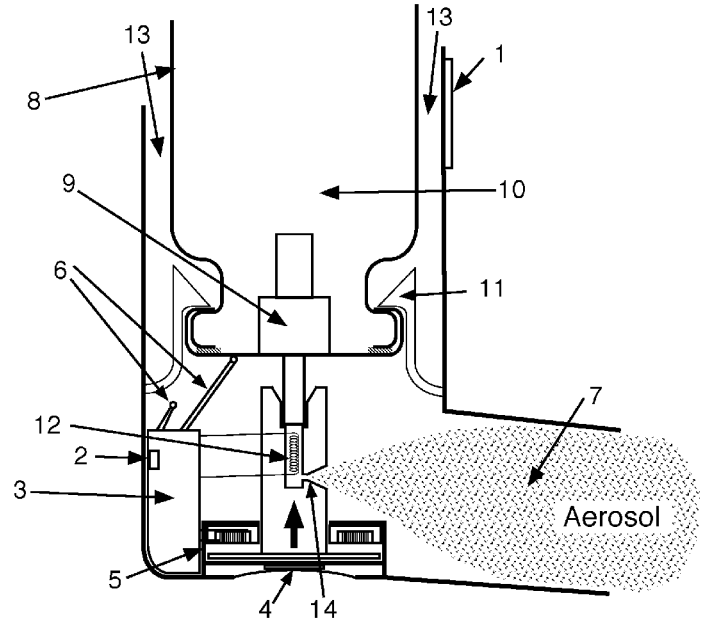

(51) Int. Cl.
*A61K 31/498* (2006.01)
*A24F 40/485* (2020.01)
*A24F 40/50* (2020.01)
*A24F 40/60* (2020.01)
*A24F 40/20* (2020.01)

(52) U.S. Cl.
CPC ............ *A24F 40/60* (2020.01); *A61K 31/465* (2013.01); *A61K 31/498* (2013.01); *A61M 15/008* (2014.02); *A61M 15/0066* (2014.02); *A24F 40/20* (2020.01); *A61M 2202/064* (2013.01); *A61M 2205/3331* (2013.01); *A61M 2205/3368* (2013.01); *A61M 2205/36* (2013.01); *A61M 2205/50* (2013.01); *A61M 2205/502* (2013.01); *A61M 2205/52* (2013.01); *A61M 2205/8206* (2013.01); *A61M 2230/42* (2013.01)

(56) References Cited

U.S. PATENT DOCUMENTS

| | | | | |
|---|---|---|---|---|
| 5,497,764 | A | * | 3/1996 | Ritson .................... G01F 13/006 128/200.14 |
| 5,906,202 | A | * | 5/1999 | Schuster ........... A61M 15/0083 128/203.23 |
| 2015/0040899 | A1 | * | 2/2015 | Spandorfer ........... A61M 16/14 128/202.27 |

* cited by examiner

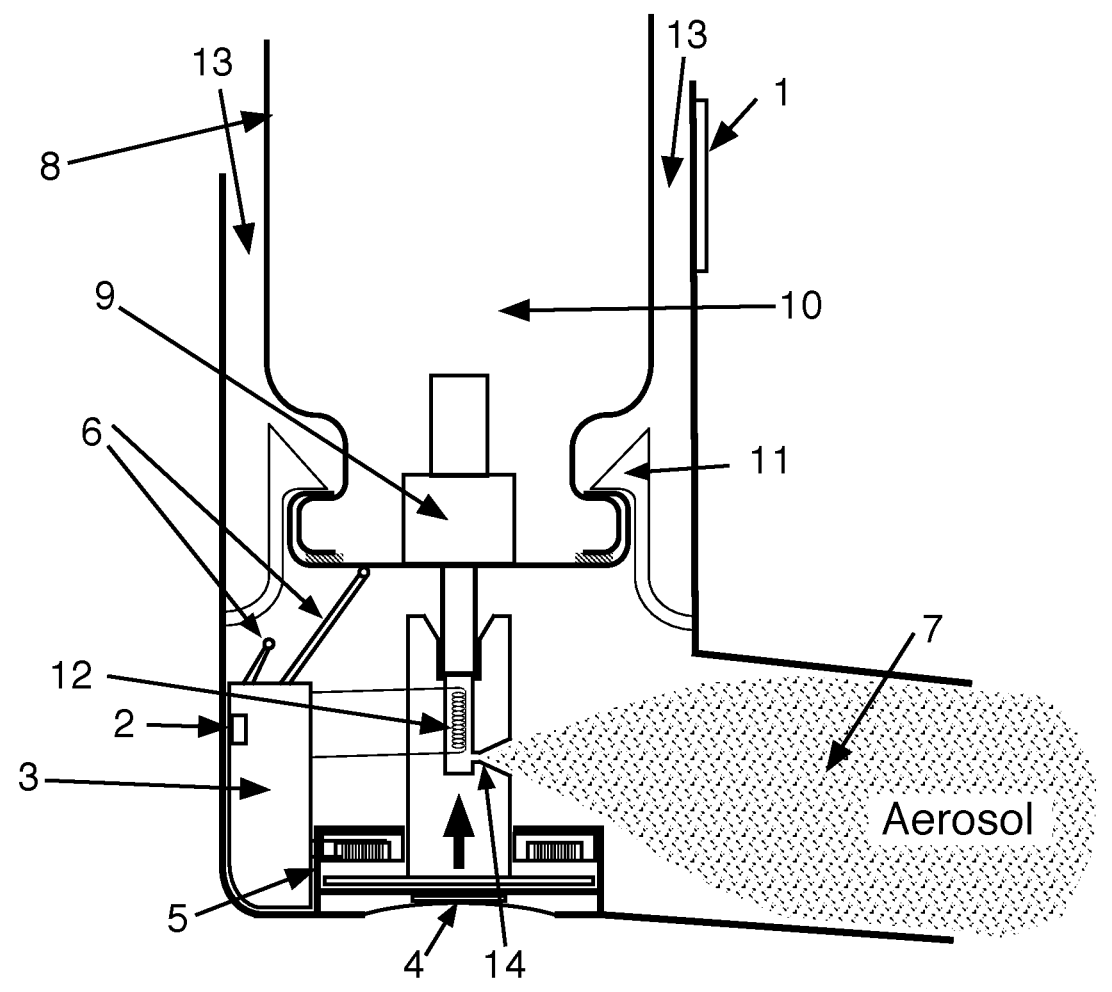

DEVICES AND CONTROL SYSTEMS FOR INHALED DRUGS

CROSS-REFERENCE TO RELATED APPLICATIONS

The present application claims priority under U.S. Application No. 62/454,843 filed Feb. 5, 2017

FIELD OF THE INVENTION

The present invention relates to methods and apparatus for electronically controlled drug inhaler devices. Specific embodiments may include but are not limited to more accurate inhaled doses, improved lung deposition of biologically-active substances, inhaler device easier to use, storage of data from producer, data from user and health care provider, program compensation for age, usage and environmental conditions to improve performance. Specific embodiments also include improvements to the medical pressurized metered dose inhaler using standard valves or improved valves.

BACKGROUND OF THE INVENTION

The typical pressurized metered dose inhaler (MDI) for delivery of aerosol drugs has many shortcomings for dose reproducibility and aerosol size distribution. Furthermore, many mechanical features of the pressurized metered dose inhaler such as orifice size and metering volume are fixed for an approved MDI. Although the combination drug/device product MDI has fixed aerosol drug formulation and fixed valve/actuator specifications the patient and environment can have significant variability changing inhaled drug treatment efficacy. For example, patients can have different disease conditions, treatment complications, age, weight, and different MDI use variables such as breath timing and actuation speed, force, etc. The MDI has many variables such as storage time, storage conditions, and pressure/temperature at the time of use effecting dose and aerosol size.

Software and/or firmware programs to control an electronically controllable MDI valve could reduce or eliminate many shortcomings of a totally mechanical MDI such as dose variation with storage or use temperature. Variations in drug aerosol size distribution and dose can change inhaled drug mass distribution in the lungs. This can be partly or totally compensated with software or firmware with a processor that can control an electromechanical MDI valve or valve actuator using data such as temperature, fluid pressure, fluid flow, doses used, time since last aerosol discharge, production date, shaking, etc. This invention with microprocessor controlled inhaler can also easily display data such as but not limited to doses used, doses remaining, expiration date or time to expiration date, programmed dose for delivery, warnings like too hot, too cold, needs shaking, needs priming dose, almost out of doses, inhaler battery low, inhaler needs to be replaced, and the like. The mechanical metered volume in the typical MDI also has variable pressure as the dose is released from the small fixed volume with changing flow and aerosol size during discharge. In this invention a partial volume discharge actuator or directly mounted electromechanical valve can reduce or eliminate this potential problem when it is controlled by a controller with the correct data inputs. Many of the non-adjustable mechanical variables in the typical MDI can be at least partly compensated for in a program and processor controlled MDI using an electromechanical valve or valve actuator. This present invention also discloses the optional heating device for a metered dose inhaler to improve aerosol formation and/or compensate for low temperature operating conditions of the MDI. This patent is different from U.S. Pat. No. 9,010,329 B2 filed Feb. 10, 2010 with one or more of the following condition sensors such as temperature, and/or pressure, flow, breath detection/activation combined with program control for valve control of the pressurized metered dose inhaler. This new patent also describes the use of a standard mechanical MDI valve and canister fitted with an electromechanical valve actuator that can be microprocessor controlled for the additional advantage of using mechanical valves that have a history of FDA or other approval(s) in other inhaler devices. The list below shows many of the advantages of a program controlled MDI with some potential applications to dry powder inhalers and nebulizers for delivery of drugs to the respiratory system. In the case of a dry powder inhaler the inhaler device program could control a powder container opener and/or electromechanical powder dispersion device. An inhaler device program in a nebulizer this program could open a drug container and/or aerosol valve(s) for nebulizer timing, gas modulation, and the like.

BRIEF SUMMARY OF THE INVENTION

The methods and apparatus in this present invention is provided to overcome one or more disadvantages of the prior art. In one embodiment, the invention directly controls a standard MDI valve of the type that is commonly used in FDA approved metered dose inhalers. The force and displacement to actuate this valve is provided by an electromechanical device that controls the timing and duration of the valve opening from the processor output using program, data inputs including possible sensors inputs. In this embodiment an electromechanical actuator can provide the program specified dose more accurately than the prior art.

In another embodiment, the invention directly controls a standard MDI valve of the type that is commonly used in FDA approved metered dose inhalers where the force and displacement to actuate this mechanical valve is provided by the user directly compressing a latching mechanism or using a lever to depress canister or set up valve for actuation. Then the program controlled actuator only triggers the valve opening with program controlled timing and duration using data from air flow breath activation and/or patient switch input.

In another embodiment, the invention directly controls a standard MDI valve of the type that is commonly used in FDA approved metered dose inhalers where the force and displacement to actuate this mechanical valve is provided by the propellant gas pressure from the previous valve actuation or other stored energy.

In another embodiment, the invention directly controls an electromechanical MDI valve similar to the types shown in U.S. Pat. No. 9,010,329 B2 instead of a standard mechanical MDI valve. This embodiment also includes additional sensors inputs and possible breath activation with program control which provides improvements over the prior art. A directly mounted valve may also eliminate the stagnant metering volume in some MDIs that need extra shaking and possible priming dose.

In additional embodiments, all the pressurized metered dose inhalers listed above a micro-heater is placed in a high flow region of the propellant/aerosol drug formulation to focus most of the heating on the discharged aerosol.

In this invention the program controlled micro-heater can have different power outputs for enhanced initial aerosol formation, increased propellant evaporation and increased solvent evaporation if ethanol or other solvent is added to the formulation. This micro-heater can compensate for low inhaler temperature and other conditions or simply improve aerosol formation. This micro-heater allows rapid heating of the aerosol drug formulation to minimize drug decomposition and minimize drug formulation separation. This is distinctly different from the vaporizer inhaler devices commonly available as electronic cigarettes (e-cigarettes, vape, and the like) where stagnant liquid is heated repeatedly in the presents of oxygen causing the separation and decomposition of many inhaled compounds.

Other additional embodiments include program control of dry powder inhalers and nebulizers. In the case of a dry powder inhaler the inhaler device program could control a powder container opener and/or electromechanical powder dispersion device. An inhaler device program for a nebulizer could open a drug formulation container and/or control aerosol valve(s) for nebulizer.

BRIEF DESCRIPTION OF THE DRAWING

FIG. 1 is a diagram depicting a standard metered dose inhaler (MDI) metering valve and can in the first embodiment where the valve is actuated entirely by the force and displacement of the electromechanical actuator. Where 1 is the display that can show doses used and/or remaining, display warnings such as over/under temperature, almost out of doses, leaking inhaler, with optional beeper warning with other display options. Where 2 is the data input/output using wire or wireless communications. Where 3 is the central processing unit for controlling the MDI, Where 4 is the user aerosol output trigger switch that can be combined with breath activation data for dose release. Where 5 is the electromechanical aerosol valve actuator controlled by the program/MDI controller. Where 6 are sensors that may include but are not limited to temperature, flow, pressure, vibration, acceleration, breath detection, breath activation and the like, where 7 is the metered aerosol or particulate matter output dose that is inhaled. Where 8 is the aerosol source container. Where 9 is the mechanical aerosol valve that is activated by 4. This valve may be a large metering valve to allow partial volume release for dose control window of operation. Where 10 is the aerosol drug formulation fluid with propellant, additives and drug or drugs. Where 11 holds aerosol can in place for electromechanical operation of mechanical valve. Where 12 is a possible heating coil for propellant and drug formulation heating to enhance aerosol formation. Where 13 is the air inlet inhaled with aerosol. Where 14 is the aerosol outlet orifice.

DETAILED DESCRIPTION OF THE INVENTION

This patent describes the use of inputs for electronic control of medical aerosol generators or inhaler devices to optimize dose, optimize dose timing, optimize aerosol/particle size, optimize inhaled drug efficacy, or a combination of two or more thereof. This can be applied to the pressurized metered dose inhaler (MDI) with many potential advantages. The MDI input sensors can include but are not limited to switch pressed by patient ready for dose, air flow sensor that can trigger breath activation through processor, temperature sensor that can measure current MDI temperature and record temperature history, and possible pressure sensor. Program outputs can include but are not limited to MDI, display data, recorded data, program data, valve control and or formulation fluid heating.

In one embodiment, the invention directly controls a standard MDI valve of the type that is commonly used in FDA approved metered dose inhalers. The force and displacement to actuate this valve is provided by an electromechanical device that controls the timing and duration of the valve opening. In this configuration a large volume metering valve or continuous output valve will be used so that the electromechanical actuator can provide the program specified dose without large pressure drop during the dose that can cause a change in the aerosol size. This configuration will include most of the potential advantages of a processor electronically controlled MDI described in this patent including but not limited to possible fluid heating to enhance aerosol size distribution. The trapped volume metering valve in this configuration may also allow the aerosol drug/propellant fluid micro-heater to create higher pressures than inside the MDI canister when it is placed between the valve and outlet orifice as seen in 14 of FIG. 1 for the drawing of this embodiment.

In another embodiment, the invention directly controls a standard MDI valve of the type that is commonly used in FDA approved metered dose inhalers where the force and displacement to actuate this mechanical valve is provided by the user directly compressing a latching mechanism or using a lever to depress canister or set up valve for actuation. Then the program controlled valve actuator only triggers the valve opening with program controlled timing and duration using data from air flow breath activation and/or patient switch input. This configuration will include most of the potential advantages of a processor electronically controlled MDI described in this patent but minimized the force and displacement energy required to operate the mechanical MDI valve because the patient will provide this energy input.

In another embodiment, the invention directly controls a standard MDI valve of the type that is commonly used in FDA approved metered dose inhalers where the force and displacement to actuate this mechanical valve is provided by the propellant gas pressure from the previous valve actuation or other energy source.

In another embodiment, the invention directly controls an electromechanical MDI valve similar to the types shown in U.S. Pat. No. 9,010,329 B2 filed Feb. 10, 2010 instead of a standard mechanical MDI valve. This embodiment also includes sensors inputs and processor to control this valve so that this configuration will include the advantages of a processor controlled MDI described in this present invention. This valve directly mounted on the aerosol canister will have the advantage of no significant pressure drop from the limited small volume of the standard MDI valve. A directly mounted valve also has the potential advantage of low operating energy and more precise timing. This valve could also eliminate the stagnant metering volume in some MDIs that need extra shaking and possible priming dose. This direct canister mounted electromechanical MDI valve may integrate better with the drug formulation micro-heater discharged from the valve as an inhalable aerosol. Furthermore, the aerosol canister mounted electromechanical valve allows placement of the heater before or after the valve. When the micro-heater is used a preferred embodiment this places the micro-heater in a propellant/aerosol drug formulation high flow region where most of this heated aerosol formulation will be discharged during the valve activation for inhaled dose. This allows rapid heating of the aerosol drug formulation to minimize drug decomposition and minimize drug formulation separation. This is distinctly different from the vaporizer inhaler commonly available as electronic cigarette type devices where stagnant liquid is heated repeatedly in the presents of oxygen causing the separation and decomposition of many inhaled compounds. In this invention the electronically controlled micro-heater can have different power outputs for enhanced initial aerosol formation, increased propellant evaporation and increased solvent evaporation if ethanol or other solvent is added to the formulation. This directly mounted electromechanical valve also allows placement of a pressure sensor to monitor propellant/formulation pressure which is not currently available in FDA approved mechanical MDI metering valves.

List of potential advantages for processor/program controlled MDI valve or valve actuator.

1. Program controlled electromechanical MDI valve with program variable open duration, dose release timing, and/or variable flow can provide better dosing by compensating for current MDI temperature, storage temperature, storage time/condition, number of doses used, pressure, flow measurement and patient data.
2. Valve opening duration, flow rate control, and other outputs for a MDI electromechanical valve or valve actuator can provide a dose programmed specifically for the patient instead of only fixed dose geometries offered by standard MDI with no compensation for operating conditions.
3. Program for multifunction display can show doses used, doses remaining, time to next dose, dose ready ("dose ready anytime today") (with optional beep or blink), days, weeks, months, left for remaining doses, time left to expiration date, inhaler too hot display (with optional beep or blink), battery low indicator (with optional beep or blink), change aerosol canister.
4. The display program can show mass of aerosol drug dose in each dose output for easy reading by patient, doctor, guardian or pharmacist.
5. The electronic valve actuator with variable opening time and possible variable flow with directly mounted electromechanical valve can maintain more constant dose using programmed digital temperature compensation which allows MDI use at high and low temperature with the same dose even in hot or cold weather.
6. Processor/program controlled MDI could also use an aerosol drug formulation/propellant fluid micro-heater in the valve actuator or part of the valve assembly to compensate for temperature to maintain aerosol size distribution especially in cold weather.
7. The MDI electronic valve actuator can also control a heated fluid (micro-heater) space after the valve and before the orifice for improved aerosol size distribution with faster propellant evaporation from smaller initial aerosols.
8. The MDI directly mounted electromechanical valve configuration allows micro-heater before or after valve and possible addition of can pressure sensor.
9. The MDI electronic valve with the addition of a pressure sensor can also compensate for pressure drop with variable opening time or duration as the MDI becomes empty.
10. The program in this MDI invention can detect mass flow changes during use from leaking MDI or blocked orifice with flow detection from micro-heater resistance (hot wire flow meter) or other fluid mass flow sensors to signal MDI problem.
11. Program can also warn of leaks using time, pressure, flow and usage data.
12. Program could prevent small orifice blockage with flow detection and/or short time extra valve opening to clear blockage.
13. The variable valve timing, duration, and opening, combined with micro-heater time/power may overcome nearly all the limitations of the standard mechanical MDI.
14. Processor/program controlled valve actuator and fluid micro-heater could replace many metering volumes, jet/orifice sizes and other geometric variables in mechanical only MDIs.
15. This invention electronically controls valve or valve actuator providing an additional form of data to processor to compensate for remaining drug formulation.
16. The electronic dose counter is triggered by program controlled aerosol valve operation without over or under count errors like add-on counter for mechanical MDIs. This provides accurate dose counter for patient, guardian, pharmacy, etc.
17. Programmed dose reminder (blink, beep, or dose available now display) could help many patients to remember to take inhaled dose on time.
18. The time to next dose in the display program will help patient planning the day.
19. The inhaler can beep or blink when it is close to the last dose or past the last dose.
20. Doses and time remaining display will help patient plan time for refill purchase.
21. Breath/dose counter can indicate and track multiple breath doses for high dose drugs.
22. A program that includes actual inhaled dose time recorder can help determine patient medication schedule compliance for doctor review.
23. A programmable MDI could use cell phone, WiFi or other communication for readable dose status or MDI compliance or MDI history and current condition.
24. This MDI invention has the easy option to be programmed at the pharmacy with patient specific dose instead of only fixed doses offered by standard MDIs. Wire or wireless communications can also be used to program patient information for best breath activation and other patient specific operation.
25. Display on the MDI can show doses remaining, time to next dose, dose ready, time left for remaining doses, time left to expiration date, inhaler too hot, battery low indicator, remind user to shake inhaler before use (with optional sound or blink).
26. This MDI invention could also be used to warn user if re-priming is required if program detects storage time or conditions that require re-priming MDI.
27. Program could respond to accelerometer or vibration detector and/or position sensor to determine adequate shaking (ready display after shaking) or remind user to shake inhaler before inhaled dose. The program could also compensate for non-shaken or inadequate shaking before use.
28. Over dose prevention can be programmed into electronic MDI not allowing additional doses until next prescribed dose. This could allow aerosol delivery of controlled substances and drugs that need to be delivered close to dose limiting toxicity.
29. Programming for low battery warning could display safe number of doses available before recharge.
30. Programming to store inhaler condition history can provide additional data for optimized inhaled dose release.

31. Program for high temperature or low temperature alarm could warn users before inhaler or drug formulations is permanently damaged in incorrect storage conditions.
32. Storage conditions that can cause permanent damage (extreme high/low temperature etc.) that can't be compensated by the MDI program and could warn the user to acquire a new MDI.

This processor/program controlled MDI technology is vastly different than electronic dose recording and reporting MDIs which do not have temperature and other compensation for accurate dose delivery from an electronically controlled valve actuator or direct electromechanical valve and possible aerosol fluid micro-heater. The inhaled aerosol size and dose is accurately controlled in the MDI invention by valve opening, duration, timing, and possible discharge heating for best indication and best lung distribution of the drug. The electronic breath activation features listed below are also critical advancements over current mechanical breath activation systems. The processor/program controlled breath activation can be patient specific air flow and/or air volume triggered which is normally fixed in mechanical breath activation MDIs.

Advantages to Electronic Breath Activation
1. Programmable breath detection or breath activation flow and volume can be adjusted for age and/or physical condition or specific lung condition of the patient.
2. The possible combination of easy user activation switch depression and breath flow activation could prevent accidental aerosol dose discharges in backpack etc.
3. Accurate breath activation air flow can be programmed as either/and/or logic combined with button activation (combination button depression flow activation could prevent accidental dose discharge).
4. Combination switch and breath detection is more likely to record actual doses taken for better dose counting and recorded inhalations.
5. The easy activation switch depression and programmable breath flow activation will help elderly and young that are challenged by the strong springs in the MDI valves.
6. The electronic breath activation eliminates coordination of breathing with depression of standard MDI valve.
7. The programmable breath activation allows slow or fast inhalation unlike some inhalers that may require fast inhalation that is difficult or impossible for some patients.
8. The electronic breath activation prevents stuck activator unlike mechanical breath activation on some MDI valves.
9. Breath flow detector can monitor and record patients respiratory condition.
10. Breath detection and breath activation threshold can be adjusted for age and/or physical condition or lung condition.
11. Electronic breath activation allows aerosol drug release at the best inhalation flow and volume for the patient.
12. An important feature of this inhaler invention is the option to program for early aerosol dose release timed for deep lung delivery before most inhaled air instead of after most of the inhaled air. This can improve peripheral lung deposition and drug aerosol lung retention which could improve current aerosol medicine and broaden the use of aerosol medicine to new drugs and treatments.

Specific inhaler products from this invention do not need to include all the features listed above. The essential feature of this electronically controlled inhaler device is to overcome one or more disadvantages of the prior art. Important embodiments include more accurate dosing, accurate dose counting, and possible temperature compensation with temperature sensing. This invention provides an easy means to incorporate many features with the processor/program controlled inhaler device.

Example 1

This example illustrates certain embodiments of the invention using the micro-heater 12 shown in FIG. 1. In this example a pressurized excipient mixture of ethanol and the drug clofazimine was forced through a tubular micro-heater heated to a power level that completely evaporated the volatile components of the aerosol excipient mixture close to the aerosol discharge region of the aerosol outlet. This demonstrated that the micro-heater embodiment of this invention can form drug dry powders that can be directly inhaled with the advantages of this dry powder formation method. This method is not limited to dry powder inhalation of dry powder formation given that lower power to the micro-heater can form different aerosol size distributions to optimize deposition of inhaled aerosols in the lungs. This example also illustrates the advantage to oxygen free, single pass, rapid heating of the biologically active material minimizing drug decomposition of the prior art of the common e-cigarette type of vaporizer.

The invention claimed is:
1. A metered dose inhaler for providing a metered dose of aerosol formulation for controlled inhaled delivery, wherein the metered dose of aerosol formulation comprises a prescribed dose of a biologically active material, wherein the aerosol formulation is pressurized in a canister by a propellant gas,
the metered dose inhaler comprising:
(a) a metering valve operable to release the aerosol formulation from the canister, wherein the metering valve is selected from the group consisting of an electromechanical valve and a mechanical valve provided with an electromechanical actuator;
(b) an aerosol outlet from which the aerosol formulation is released for inhalation, arranged downstream of the metering valve;
(c) at least one sensor including an inhaler temperature sensor; and
(d) a controller, the controller comprising:
(i) a digital processor operable to control the functions of the metered dose inhaler to release the metered dose of aerosol formulation from the canister;
(ii) a memory operable to store data for generating the metered dose of the aerosol formulation based on sensed operating conditions including ambient temperature;
(iii) a program operable to control the digital processor to operate the metered dose inhaler to release the metered dose of aerosol formulation from the electromechanical metering valve or electromechanical actuator of the metering valve under sensed operating conditions including the ambient temperature sensed by the temperature sensor.
2. The metered dose inhaler according to claim 1, wherein an aerosol generating pressure is provided by an arrangement in the canister selected from (a) vapor phase propellant gas in equilibrium with propellant gas dissolved in the aerosol formulation, (b) propellant gas pressure on a side of an aerosol formulation barrier opposite the aerosol formulation, (c) propellant gas dissolved in the aerosol formulation, (d) propellant gas in a vapor phase, and (d) propellant gas in both the aerosol formulation and in a vapor phase above the aerosol formulation.

3. The metered dose inhaler according to claim 1, wherein the propellant gas is selected from the group consisting of nitrogen, carbon dioxide, difluoromethane, 1,1,1,2-tetrafluoroethane, 1,1,1,2,3,3,3-heptafluoropropane, air, and a mixture thereof.

4. The metered dose inhaler according to claim 1, further comprising at least one additional temperature sensor operable to sense a temperature selected from air inhaled into the inhaler, air inhaled through the inhaler, outlet temperature, and inhaler aerosol source container temperature or other inhaler temperatures.

5. A metered dose inhaler for providing a metered dose of aerosol for controlled inhaled delivery of biologically active material, the metered dose of aerosol containing a prescribed dose of biologically active material, aerosolized with a pressurized propellant, the metered dose inhaler comprising:
(a) a metering valve operable to release the metered dose of aerosol with a pressurized propellant from a canister, wherein the metering valve is selected from the group consisting of an electromechanical valve and a mechanical valve provided with an electromechanical actuator;
(b) an air flow sensor operable to sense a user's inhalation air flow;
(c) an aerosol outlet from which the aerosol is released for inhalation, arranged downstream of the metering valve;
(d) at least one a temperature sensor operable to sense the metered dose inhaler temperature; and
(e) a controller, the controller comprising:
(i) a digital processor operable to control the metering valve to release a metered dose of the aerosol;
(ii) a memory operable to store data for generating the metered dose of aerosol;
(iii) a program operable to control the digital processor to operate the metering valve to release the metered dose of aerosol as a function of inhaled air flow sensed by the air flow sensor and the metered dose inhaler temperature sensed by the temperature sensor.

6. The metered dose inhaler according to claim 5, wherein the controller is operable to release a dose when a predetermined air flow is sensed, or is operable to release a dose at a time and air flow computed by the digital processor from a signal sensed by the air flow sensor.

7. The metered dose inhaler according to claim 5, wherein the air flow sensor is operable to measure pulmonary function data, and wherein the digital processor is operable to determine aerosol dose release time and flow rate, aerosol drug formulation fluid heating operation, metering valve opening duration, or a need for multiple doses.

8. The metered dose inhaler according to claim 5, further comprising a fluid flow sensor between the metering valve and aerosol outlet, and optionally wherein the fluid flow sensor may also comprise an aerosol heater.

9. The metered dose inhaler according to claim 8, wherein the fluid flow sensor is an electrically resistive heater operable to heat a metered dose of aerosol.

10. The metered dose inhaler according to claim 9 wherein the program is operable to control the heater power and measure flow by calculating changes in heater resistance during dose release, wherein different heater power levels are operable to compensate for low temperature aerosol by heating the aerosol to control dose, aerosol size distribution, propellant evaporation, and aerosol physical properties.

11. The metered dose inhaler according to claim 8, further comprising an aerosol flow sensor operable to determine malfunctioning of the inhaler device.

12. The metered dose inhaler according to claim 5, wherein the program is operable to display or transmit data to a user, health care provider, guardian, or pharmacist.

13. A metered dose inhaler for providing a metered dose of aerosol for controlled inhaled delivery of a biologically active material, the metered dose of aerosol containing a prescribed dose of biologically active material, aerosolized with a pressurized propellant, and the aerosol having a controlled aerosol size distribution, the metered dose inhaler comprising:
(a) a metering valve operable to release a metered dose of aerosol with a pressurized propellant from a canister, wherein the metering valve is selected from the group consisting of an electromechanical valve and a mechanical valve provided with an electromechanical actuator;
(b) a heater arranged downstream of the metering valve;
(c) an aerosol outlet from which the aerosol is released for inhalation, arranged downstream of the heater;
(d) at least one temperature sensor operable to sense the metered dose inhaler temperature; and
(e) a controller, the controller comprising:
(i) a digital processor operable to control the metering valve to release a metered dose of the aerosol from the canister and operable to actuate the heater to heat the aerosol released by the metering valve;
(ii) a memory operable to store data for generating the metered dose of aerosol having a predetermined size distribution based on the metered dose inhaler temperature;
(iii) a program operable to control the digital processor to operate the metering valve and the heater to release the metered dose of aerosol having the predetermined size distribution from the aerosol outlet as a function of the metered dose inhaler temperature sensed by the temperature sensor.

14. The metered dose inhaler according to claim 13, wherein the metering valve comprises an electromechanical valve.

15. The metered dose inhaler according to claim 13, wherein the metering valve comprises a mechanical valve provided with an electromechanical actuator.

16. The metered dose inhaler according to claim 13, wherein the memory includes an electronic dose counter that is triggered by operation of the metering valve.

17. The metered dose inhaler according to claim 13, comprising a user dose trigger to initiate operation of the controller to generate the prescribed dose of the biologically active material in aerosol form.

18. The metered dose inhaler according to claim 13, further comprising an air flow sensor operable to sense a user's inhaled air flow rate through the inhaler, wherein the controller is operable to release a dose when a predetermined air flow is measured or is operable to release a dose at a time and flow calculated by the program from the air flow sensor output.

19. The metered dose inhaler according to claim 13, wherein the biologically active material is selected from corticosteroids, salbutamol, antibiotics, vaccines, anticancer agents, cannabinoid compounds, and nicotine drugs.

20. The metered dose inhaler according to claim 12, wherein the data includes user related data, health care provider related data, manufacturer control data, inhaler operation data, and time data.

\* \* \* \* \*